United States Patent [19]

Marhold

[11] Patent Number: 5,484,932
[45] Date of Patent: Jan. 16, 1996

[54] HALOGENATION PROCESSES IN ADVANTAGEOUS SOLVENTS, AND NOVEL BISTRIFLUOROMETHYL-POLYFLUOROALKOXYBENZENES

[75] Inventor: Albrecht Marhold, Leverkusen, Germany

[73] Assignee: Bayer Aktiengesellschaft, Leverkusen, Germany

[21] Appl. No.: 253,188

[22] Filed: Jun. 2, 1994

Related U.S. Application Data

[63] Continuation of Ser. No. 52,420, Apr. 15, 1993, abandoned.

[30] Foreign Application Priority Data

Apr. 27, 1992 [DE] Germany ............ 42 13 850.7

[51] Int. Cl.⁶ .................. C07D 213/26; C07C 41/22; C07C 43/205
[52] U.S. Cl. ............. 546/346; 204/157.69; 204/157.71; 204/157.92; 204/157.99; 568/655; 568/656; 568/779; 570/144; 570/197
[58] Field of Search .............................. 570/197, 206, 570/207, 144; 568/779, 655, 656; 546/346; 204/157.69, 157.71, 157.92, 157.99

[56] References Cited

U.S. PATENT DOCUMENTS

| | | |
|---|---|---|
| 2,516,403 | 7/1950 | McBee et al. . |
| 3,546,302 | 12/1970 | Asadorian et al. ............ 568/779 |
| 4,024,192 | 5/1977 | Benninger et al. . |
| 4,133,837 | 1/1979 | Markley ............ 570/197 |
| 4,719,298 | 1/1988 | Jeromin et al. ............ 546/346 |
| 4,935,562 | 6/1990 | Okisaki et al. ............ 570/206 |
| 5,157,169 | 10/1992 | Patton ............ 570/206 |

FOREIGN PATENT DOCUMENTS

| | | |
|---|---|---|
| 2350803 | 4/1975 | Germany . |
| 240031 | 9/1990 | Japan ............ 570/197 |

OTHER PUBLICATIONS

Aver'yano et al "Journal of Organic Chemistry of the USSR", vol. 26, No. 9, Part 2, Sep. 1990, pp. 1261–1264, A translation provided by applicants in parent.

V. A. Aver'Yanov, Zh. Org. Khim., 23, No. 11, 2407–2412 (1987).

*Journal of Organic Chemistry of the USSR*, vol. 26, No. 9, Part 2, Sep. 1990; "The Nature of the Attacking Particle Responsible for the Selective Action of Aromatic Solvents on Free-Radical Chlorination", pp. 1261–1264+"contents" page.

*Primary Examiner*—Joseph E. Evans
*Attorney, Agent, or Firm*—William C. Gerstenzang; Sprung Horn Kramer & Woods

[57] ABSTRACT

Compounds such as

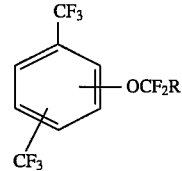

wherein R is F, $CF_3$, $CF_2H$, $CHF\ CF_3$ or $CF_2\ CF_3$, as well as related compounds containing chlorine, are used as solvents in halogenation processes.

5 Claims, No Drawings

HALOGENATION PROCESSES IN ADVANTAGEOUS SOLVENTS, AND NOVEL BISTRIFLUOROMETHYL-POLYFLUOROALKOXYBENZENES

This application is a continuation of application Ser. No. 052,420, filed Apr. 15, 1993, now abandoned.

The present invention relates to halogenation processes which are carried out in the presence of advantageous solvents, and to novel, chlorine-free bistrifluoromethylpolyfluoroalkoxybenzenes.

Halogenation reactions can often only be carried out successfully in the presence of solvents. Solvents for this purpose must not, under the conditions applied, themselves be halogenated, and they should not interrupt radical chain mechanisms, as halogenation reactions are often reactions involving radicals.

The industrial requirements made of solvents for halogenation processes are met effectively by carbon tetrachloride, and this solvent, therefore, has been widely used hitherto. However, carbon tetrachloride has the major drawback that, because of its toxicity and volatility, a major effort is required to meet the regulations on occupational hygiene and environmental protection. There is therefore a need for solvents for halogenations, where such an effort is required to a lesser extent or not at all.

We have found halogenation processes which are characterised in that the solvent used therein comprises one or more compounds of the formula (I)

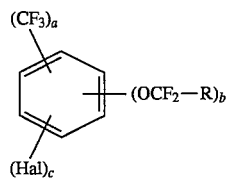

in which
R represents fluorine, chlorine, $CF_3$, $CF_2H$, $CF_2Cl$, $CHFCF_3$, $CF_2CF_3$ or $CFClCF_3$,
Hal represents fluorine or chlorine,
a represents zero, 1, 2 or 3,
b represents zero, 1 or 2, and
c represents zero or, in the case Hal=fluorine, can also represent 1, 2 or 3, and, in the case Hal= chlorine, can also represent 1,
where a and b do not represent zero simultaneously and the sum a+b+c is at most 6.

In the formula (I), preferably,
R represents fluorine, $CF_3$, $CF_2H$, $CHFCF_3$ or $CF_2CF_3$,
Hal represents fluorine or chlorine,
a represents zero, 1 or 2,
b represents zero or 1, and
c represents zero or 1,
where a and b do not represent zero simultaneously.

In the formula (I), particularly preferably,
R represents fluorine, $CF_2H$ or $CHFCF_3$,
Hal represents chlorine,
a represents zero or 2,
b represents zero or 1, and
c represents zero or 1,
where a and b do not represent zero simultaneously, and the sum a+b+c is at most 3.

It is further preferred that in the case of 2 $CF_3$ groups being present, these are in meta positions with regard to one another and, in the case of an $OCF_2$-R group and further substituents being present, said further substituents are in meta or para positions with regard to the $OCF_2$-R group.

The present invention also relates to novel, chlorine-free bistrifluoromethyl-polyfluoroalkoxybenzenes of the formula (II)

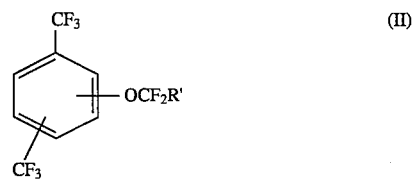

in which
R' represents fluorine, $CF_3$, $CF_2H$, $CHFCF_3$ or $CF_2CF_2CF_3$.

In the formula (II), R' preferably represents fluorine, $CF_2H$ or $CHFCF_3$.

In the formula (II), the three substituents are preferably arranged in the 1,3,4- or 1,3,5-position on the benzene ring.

The compounds of the formula (I), with the exception of the compounds of the formula (II), are commercially available or can be prepared according to known methods or by methods similar to those known (cf. e.g. Pavlat and Leffler, Aromatic Fluorine Compounds, New York (1962), p. 47 et seq. and European Published specification 0 180 818, in particular Claim 11).

Compounds of the formula (II) can be prepared if compounds of the formula (III)

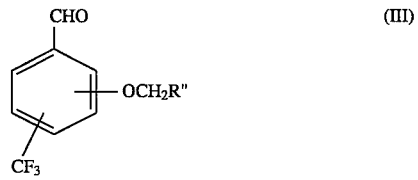

in which
R" represents hydrogen, $CFCF_3$ or $CHFCF_3$
are first chlorinated with phosphorus pentachloride/chlorine, and the chlorination products are reacted with anhydrous hydrogen fluoride or antimony trifluoride, in the presence of a catalyst if required.

Compounds of the formula (II) can also be prepared if a phenol of the formula (IV)

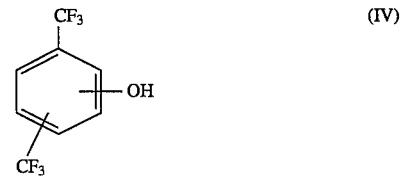

is reacted with a $C_2$-$C_3$-perfluoroolefin in the presence of a base (e.g. aqueous sodium hydroxide).

The halogenations according to the invention are preferably chlorinations and brominations. Possible halogenating agents are e.g. chlorine, sulphuryl chloride, bromine and N-bromosuccinimide. The reaction parameters (e.g. proportions of halogenating agents to substrate, temperatures, pressures, catalysts if required, etc.) can be chosen as usual for such reactions.

For example, the solvent to be used according to the invention can be used in amounts from 5 to 1000% by weight, based on the substance to be halogenated. Preferably this amount is 20 to 500% by weight. It is possible, for example, to introduce the substance to be halogenated together with the solvent to be used according to the invention as an initial charge, and then to meter in the halogenating agent. It is also possible to introduce the solvent, together with a small amount of the substance to be halogenated if required, as an initial charge, and to meter all or most of the substance to be halogenated into the reaction vessel simultaneously with the halogenating agent. The substance to be halogenated and the halogenating agent can also be combined in any other way desired.

It is possible to use the halogenating agent in the process according to the invention in, for example, the stoichiometrically required amount or in excess, for example up to an excess of 100 mol %.

As the solvents to be used according to the invention have higher boiling points than has carbon tetrachloride, unpressurised processes can be carried out within a wider temperature range than has been possible hitherto. In general, it is sufficient to carry out the halogenations according to the invention at atmospheric pressure and temperatures up to the boiling point of the solvent used. In particular cases the halogenation, at lower or higher temperatures than that corresponding to the boiling point of the solvent used (at atmospheric pressure), can also be carried out under pressure, for example if sluggishly reacting substances are to be halogenated and/or improved mass transfer of the halogenating agent is to be achieved. Commonly, reaction temperatures in the range from 0° to 180° C. can be applied.

If required, the catalysts generally used for the halogenation in question can be employed, for instance halogenations of the ring making use of Friedel-Crafts catalysts such as $FeCl_3$, iron and $TiCl_4$, and side chain halogenations making use of free-radical initiators such as benzoyl peroxide, di-tert.-butyl peroxide and azo-bis-isobutyronitrile.

Working up the reaction mixtures obtained and recovery of the solvent employed according to the invention can be carried out in a manner known per se, for example by distillation.

The present invention makes it possible to perform a wide range of halogenations. For example, it is thus possible to carry out the chlorination or bromination of benzene derivatives in the ring, of alkyl- and polyalkyl-benzene derivatives in the ring and/or in the side chain, of naphthalenes in the ring, or of heteroaromatics, e.g. picoline, in the side chain. The solvents to be employed according to the invention can also be used advantageously in the chlorination and bromination of aliphatic and cycloaliphatic compounds.

It is preferable to carry out, in the manner according to the invention, the chlorination of those hydrogen atoms which are contained in side chains, of the types hydrocarbon, halogenohydrocarbon, alkyl ether and/or halogenoalkyl ether of aromatic compounds.

The process according to the invention has a number of surprising advantages. The solvents to be employed are less toxic and less volatile than carbon tetrachloride, and therefore require virtually no special effort in the field of occupational hygiene and environmental protection. In many cases, they can be recovered and be reused for chlorinations virtually as many times as wanted. Although the solvents to be employed according to the invention, in particular those of the formula (II), carry hydrogen atoms on the aromatic ring which, theoretically, are susceptible to halogenation, no such chlorinations in the ring are observed under the conditions usually to be applied in the process according to the invention.

EXAMPLES

Example 1

A chlorination apparatus was charged with 50 ml of 4-chloro-trifluoromethoxybenzene, and 1 g of potassium chloride and 1 g of phosphorus trichloride were added. At 80° C., a solution of 2 g of azobisisobutyronitrile in 120 g of 4-chloroanisole was then metered in from a dropping funnel, and chlorine was introduced at the same time. The completion of chlorination was determined by gas chromatography. In the course of the subsequent distillation, 96% by weight of the 4-chloro-trifluoromethoxybenzene employed as the solvent were recovered, and 186 g of 4-chloro-trichloromethoxybenzene (boiling point 122° to 126° C. at 16 mbar, refractive index $n_D^{20}$ 1.5565) were obtained as the chlorination product, corresponding to a yield of 89.8% of theory. It was possible to reuse the recovered 4-chloro-trifluoromethoxybenzene, together with a small intermediate fraction, for this chlorination.

Example 2

0.5 g of potassium chloride and 10 g of difluoromethoxybenzene in 100 ml of 1,3-bistrifluoromethylbenzene were introduced as the initial charge, and chlorine was then introduced at 100° C. with UV irradiation. In the course of an hour, another 20 g of difluoromethoxybenzene were metered in. After chlorine uptake was complete, the reaction mixture was purged with nitrogen and subsequently distilled. 35.5 g of chlorodifluoromethoxybenzene were isolated (boiling point 144° C., refractive index $n_D^{20}$ 1.4479).

Example 3

The same procedure was used as in Example 2, but instead of the difluoromethoxybenzene, 100 g of 2,2,2-trifluoroethoxybenzene were used. Of this amount, 10 g were introduced as the initial charge, and the remaining 90 g were metered in together with the chlorine. 101.5 g of 1,1-dichloro-2,2,2-trifluoroethoxybenzene were isolated (boiling point 77° to 80° C. at 20 mbar, refractive index $n_D^{20}$ 1.4615).

Example 4

A stirred apparatus equipped with a chlorine inlet, a metering device, a multiple-coil condenser and a gas outlet was charged with 600 g of 1,3-bistrifluoromethylbenzene at 110° C., a solution of 18 g of azobisisobutyronitrile in 900 g of benzodioxole was then metered in slowly (75 to 80 g per hour) and, at the same time, 100 to 105 g of chlorine per hour were introduced. The reaction was exothermic and was maintained at 110° C. by removing the heating bath. After all of the benzodioxole and chlorine had been metered in, chlorine was passed in for another 30 minutes, the mixture was then purged with nitrogen, and distilled. After taking off 630 g of a first fraction (1,3-bistrifluoromethylbenzene and reusable chlorination material), 1240 g of 2,2-dichlorobenzodioxole were obtained (boiling point 81° to 90° C. at 12 mbar).

Example 5

A chlorination apparatus was charged with 150 g of 3,5-bistrifluormethyl-1,1,2,3,3,3-hexafluoropropoxybenzene, and 50 g of 4-methyl-2,2-difluorobenzodioxole together with 54 g of N-bromosuccinimide and 0.5 g of azobisisobutyronitrile were heated to 80° to 85° C. for 8 hours. After cooling, the solid was filtered off with suction and washed with a small amount of hexane. By means of distillation, the solvent (3,5-bistrifluoromethyl-1,1,2,3,3,3-hexafluoropropoxybenzene) was recovered and, as a further fraction, 59.3 g of 4-bromomethyl-2,2 -difluorobenzodioxole were obtained as the bromination product (boiling point 102° to 104° C. at 20 mbar).

Example 6

400 g of 4-fluorophenol in 400 ml of 3,5-bistrifluoromethyl-trifluoromethoxybenzene were introduced as the initial charge, and 2 g of iron shavings were added. 280 g of chlorine were then introduced at 20° to 25° C. The mixture was stirred for another 20 minutes, nitrogen was used to purge any chlorine remaining and the hydrogen chloride produced, and the batch, after filtration, was subjected to distillation. After recovery of the solvent (3,5-bistrifluoromethyl-trifluoromethoxybenzene), 449 g of 2-chloro-4-fluorophenol having a boiling point of 63° to 65° C. at 15 mbar and a refractive index $n_D^{20}$ of 1.5304 were obtained.

Example 7

(preparation example)

490 g of 3,5-bistrifluoromethyl-phenol in 100 ml of acetone, together with 50 g of 50% by weight aqueous sodium hydroxide, were introduced as the initial charge, and hexafluoropropene was introduced at 25° C. until saturation was achieved. The batch was then diluted with 1 l of water, the organic phase was separated, dried and distilled. 673 g of 3,5-bistrifluoromethyl-phenyl-1,1,2,3,3,3-hexailuoropropyl ether (boiling point 65° to 70° C. at 22 mbar, refractive index $n_D^{20}=1.3560$) were obtained.

Example 8

The solvent obtained according to Example 7 was treated with chlorine for 3 hours at reflux temperature with UV irradiation. In a subsequent analysis by gas chromatography, no chlorination products could be found.

Example 9

200 g of 2,3-dichloro-benzo-1,4-dioxene in 500 ml of 1,4-bistrifluoromethylbenzene were introduced as the initial charge and heated to 110° C. Chlorine was introduced under UV irradiation, and the progress of chlorination was checked by means of gas chromatographic analysis. After the reaction was complete, the chlorine supply was interrupted, the batch was purged with nitrogen and subsequently distilled. 240 g of 2,2,3,3-tetrachloro-benzo- 1,4-dioxene having a boiling point of 140° to 142° C. at 20 mbar and a melting point of 88° to 92° C. were obtained.

Example 10

(preparation example)

An alloy steel autoclave was charged with 1000 g of hydrogen fluoride and 10 ml of titanium tetrachloride, and a solution of 250 g of 2,5-bistrifluoromethyl-phenol in 800 ml of fluorotrichloromethane was metered in. The mixture was then heated to 130° C. for 7 hours and the hydrogen chloride produced was vented via a valve. After cooling down, the hydrogen fluoride still remaining, together with fluorotrichloromethane, was distilled from the autoclave, and the fluorotrichloromethane phase was separated from the distillate. The hydrogen fluoride was returned to the autoclave and, together with the residue remaining there, with the addition of a further 5 ml of titanium tetrachloride was heated to 130° C. for another 5 hours. After the autoclave contents had been discharged onto ice, the resulting organic phase was separated and distilled. This gave 195 g of 3,5-bistrifluoromethyltrifluoromethoxybenzene (boiling point 137° to 138° C.).

What is claimed is:

1. A process for the chlorination or bromination of a side-chain of an aromatic or heterocyclic compound which comprises reacting said compound with a chlorinating agent or a brominating agent in a solvent comprising one or more compounds of the formula I

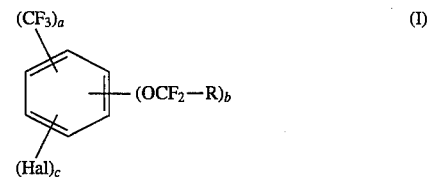

in which
R represents fluorine, chlorine, $CF_3$, $CF_2H$, $CF_2Cl$, $CHFCF_3$, $CF_2CF_3$ or $CFClCF_3$,
Hal represents fluorine or chlorine,
a represents zero, 1, 2 or 3,
b represents zero, 1 or 2, and
c represents zero or, in the case Hal=fluorine, can also represent 1, 2 or 3, and, in the case Hal=chlorine, can also represent 1,
where a and b do not represent zero simultaneously and the sum a+b+C is at most 6 and wherein the solvent is not itself chlorinated or brominated in the process.

2. The process of claim 1, in which in the formula (I)
R represents fluorine, $CF_3$, $CF_2H$, $CHFCF_3$ or $CF_2CF_3$,
Hal represents fluorine or chlorine,
a represents zero, 1 or 2,
b represents zero or 1, and
c represents zero or 1,
where a and b do not represent zero simultaneously.

3. The process of claim 1, in which in the formula (I), in the case of two $CF_3$ groups being present, these are in meta positions with regard to one another and, in the case of an $OCF_2$-R group and further substituents being present, said further substituents are in meta or para positions with regard to the $OCF_2$-R group.

4. The process of claim 1, in which the halogenating agent used is selected from the group consisting of chlorine, sulphuryl chlorine, bromine and N-bromosuccinimide.

5. The process of claim 1, in which the compounds of the formula (I) are used in amounts from 5 to 1000% by weight, based on the compound to be halogenated.

* * * * *

REEXAMINATION CERTIFICATE (4061st)
United States Patent [19]
Marhold

[11] B1 5,484,932
[45] Certificate Issued Apr. 25, 2000

[54] HALOGENATION PROCESSES IN ADVANTAGEOUS SOLVENTS, AND NOVEL BISTRIFLUOROMETHYL-POLYFLUOROALKOXYBENZENES

[75] Inventor: Albrecht Marhold, Leverkusen, Germany

[73] Assignee: Bayer AG, Leverkusen-Bayerwerk, Germany

Reexamination Request:
No. 90/005,228, Jan. 22, 1999

Reexamination Certificate for:
Patent No.: 5,484,932
Issued: Jan. 16, 1996
Appl. No.: 08/253,188
Filed: Jun. 2, 1994

Related U.S. Application Data

[63] Continuation of application No. 08/052,420, Apr. 15, 1993, abandoned.

[30] Foreign Application Priority Data

Apr. 27, 1992 [DE] Germany ............... 42 13 850

[51] Int. Cl.$^7$ ............... C07C 41/22; C07C 25/02
[52] U.S. Cl. ............... 568/656; 570/144; 570/197; 204/157.92; 204/157.99
[58] Field of Search ............... 568/655, 656; 570/144, 197; 204/157.92, 157.99

[56] References Cited

U.S. PATENT DOCUMENTS

| | | | |
|---|---|---|---|
| 2,516,403 | 7/1950 | McBee et al. | 260/612 |
| 3,546,302 | 12/1970 | Asadorian et al. | 260/619 |
| 4,024,192 | 5/1977 | Benninger et al. | 260/611 |
| 4,133,837 | 1/1979 | Markley | 260/651 |
| 4,719,298 | 1/1988 | Jeromin et al. | 544/182 |
| 4,935,562 | 6/1990 | Okisaki et al. | 520/210 |
| 5,157,169 | 10/1992 | Patton | 570/143 |

FOREIGN PATENT DOCUMENTS

| | | | |
|---|---|---|---|
| 2350803 | 4/1975 | Germany | C07C 43/18 |
| 2240031 | 9/1990 | Japan | 25/2 |
| 675122 | 8/1990 | Switzerland | C07D 317/46 |

OTHER PUBLICATIONS

V.A. Aver'Yanov, "Competing Chlorination of 1,1–Dichloroethane and Chlorobenzene" English Translation from Zh. Org. Khim., 23, No. 11, 2407–2412 (Nov. 1987). Original article submitted Jan. 21, 1996.

V.A. Aver'Yanov et al., Journal of Organic Chemistry in USSR, vol. 26, No. 9, Part 2, Sep. 1990, "The Nature of the Attacking Particle Responsible for the Selective Action of Aromatic Solvents on Free–Radical Chlorination", pp. 1261–1264 plus "contens" page.

Chupp and Smith. "Synthesis of 2/6–(Polychloromethyl)pyridine–carboylates" J. Heterocyclic Chem., vol. 25, pp. 1785–1792 (Nov./Dec. 1988).

*Primary Examiner*—John Kight

[57] ABSTRACT

Compounds such as

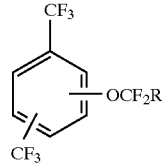

wherein R is F, $CF_3$, $CF_2H$, $CHF\ CF_3$ or $CF_2\ CF_3$, as well as related compounds containing chlorine, are used as solvents in halogenation processes.

REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–5, dependent on an amended claim, are determined to be patentable.

New claim 6 is added and determined to be patentable.

1. A process for the chlorination or bromination of a side-chain of an [aromatic or heterocyclic] *alkylbenzene derivative, polyalkylbenzene derivative, alkyl ethers of a benzene derivate or halogenoalkyl ether of a benzene derivative* compound which comprises reacting said compound with a chlorinating agent or a brominating agent in a solvent comprising one or more compounds of the formula I

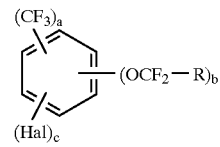

in which
R represents fluorine, chlorine, $CF_3$, $CF_2H$, $CF_2Cl$, $CHFCF_3$, $CF_2CF_3$ or $CFClCF_3$,
Hal represents fluorine or chlorine,
a represents zero, 1, 2 or 3,
b represents zero, 1 or 2, and
c represents zero or, in the case Hal=fluorine, can also represent 1, 2 or 3, and, in the case Hal=chlorine, can also represent 1,
where a and b do not represent zero simultaneously and the sum a+b+C is at most 6 and wherein the solvent is not itself chlorinated or brominated in the process.

6. *The process of claim 1, wherein*
*R represents fluorine, $CF_2H$ or $CHFCF_3$,*
*Hal represents chlorine,*
*a represents zero or 2,*
*b represents zero or 1, and*
*c represents zero or 1,*
*where a and b do not represent zero simultaneously and the sum a+b+c is at most 3.*

\* \* \* \* \*